United States Patent
Traub et al.

(10) Patent No.: US 10,429,518 B2
(45) Date of Patent: Oct. 1, 2019

(54) SYSTEM AND METHOD FOR THE DETERMINATION OF A DOSE IN RADIOTHERAPY

(71) Applicant: SURGICEYE GMBH, München (DE)

(72) Inventors: Joerg Traub, München (DE); Philipp Matthies, München (DE); Matthias Keicher, München (DE)

(73) Assignee: SURGICEYE GMBH, München (DE)

( * ) Notice: Subject to any disclaimer, the term of this patent is extended or adjusted under 35 U.S.C. 154(b) by 0 days.

(21) Appl. No.: 16/070,698

(22) PCT Filed: Jan. 18, 2017

(86) PCT No.: PCT/EP2017/050998
§ 371 (c)(1),
(2) Date: Jul. 17, 2018

(87) PCT Pub. No.: WO2017/125443
PCT Pub. Date: Jul. 27, 2017

(65) Prior Publication Data
US 2019/0018149 A1    Jan. 17, 2019

(30) Foreign Application Priority Data

Jan. 18, 2016   (DE) .................. 10 2016 100 713

(51) Int. Cl.
*G01T 1/161* (2006.01)
*G01T 1/02* (2006.01)
(Continued)

(52) U.S. Cl.
CPC ............ *G01T 1/161* (2013.01); *A61N 5/1048* (2013.01); *A61N 5/1071* (2013.01); *G01T 1/02* (2013.01);
(Continued)

(58) Field of Classification Search
CPC .. A61N 5/1067; A61N 5/1071; A61N 5/1615; A61N 5/1049; A61N 5/1044;
(Continued)

(56) References Cited

U.S. PATENT DOCUMENTS 5,844,241 A    12/1998  Liu et al.
8,239,002 B2 *  8/2012  Neustadter ........... A61N 5/1049
                                                250/303
(Continued)

OTHER PUBLICATIONS

International Search Report and Written Opinion dated Apr. 12, 2017 for PCT Application No. PCT/EP2017/050998.

*Primary Examiner* — David P Porta
(74) *Attorney, Agent, or Firm* — Moser Taboada

(57) ABSTRACT

An image generating apparatus for image generation and dose calculation is provided. The image generating apparatus includes a movable detector for detecting nuclear radiation during a detection period and an evaluation system. The evaluation system includes an interface system for transmitting detector data to the evaluation system. The detector data include information about the detected radiation for image generation. The evaluation system further includes a data memory portion for storing the detector data. The evaluation system further includes a program memory portion with a program for repeatedly determining at least one quality value with respect to image generation during the detection period. The image generating apparatus includes an output system including at least one output unit. The at least one output unit includes one output unit for outputting an instruction to a user for further moving the detector in dependence of the detector data. The instruction relates to at least a part of the remaining detection period.

17 Claims, 7 Drawing Sheets

(51) Int. Cl.
*A61N 5/10* (2006.01)
*G01T 1/16* (2006.01)

(52) U.S. Cl.
CPC .... *G01T 1/1603* (2013.01); *A61N 2005/1021* (2013.01); *A61N 2005/1076* (2013.01)

(58) Field of Classification Search
CPC .......... A61N 5/1048; A61N 2005/1076; A61N 5/1047; A61N 2005/1021; G01T 1/02; G01T 1/1603; G01T 1/161
See application file for complete search history.

(56) References Cited

U.S. PATENT DOCUMENTS

| | | |
|---|---|---|
| 8,295,910 B1 | 10/2012 | Weisenberger et al. |
| 2008/0214933 A1* | 9/2008 | Von Busch .......... A61B 5/0059 600/431 |
| 2009/0180589 A1* | 7/2009 | Wang .................. A61N 5/10 378/65 |
| 2014/0163302 A1 | 6/2014 | Fox et al. |
| 2014/0163368 A1* | 6/2014 | Rousso ................ A61B 6/037 600/436 |

* cited by examiner

SYSTEM AND METHOD FOR THE DETERMINATION OF A DOSE IN RADIOTHERAPY

The present invention relates to systems and methods for monitoring therapeutic substances applied to a body, wherein the substance comprises a radionuclide, and the apparatus comprises a nuclear detector. Specific embodiments of the invention relate to apparatuses and methods for determining a dose of a therapeutic substance which comprises a therapeutic radionuclide or a therapeutic substance which is labelled additionally with a radionuclide.

BACKGROUND

In medical therapy using therapeutic substances which are administered to a body, aimed at a particular local target such as an organ or a lesion in an organ, it is of substantial interest to know how the administered substance is accumulating in the body, and especially if the therapeutic substance is accumulated in the intended target region. The latter may be a lesion in an organ, such as a tumor, or a certain functional structure in an organ.

The former is inherently clear for the administration of a therapeutic substance which comprises a radionuclide intended for the treatment of a lesion in an organ, in particular of a tumor. In this case, it is of particular interest to be able to control or monitor where the radionuclide accumulates in the body, because it is intended to radiate only the target area and to minimize the exposure and thus the damage to all other regions of the body. Another case pertains to the administration of a chemical substance, such as in chemotherapy, which is not radioactive per se, but wherein its molecules are labelled with an additional radionuclide which serves the purpose of enabling the monitoring of the distribution of the therapeutic substance in the body by monitoring the emitted radiation from an outside of the body.

Various techniques have been proposed to determine localized concentrations of radioactive substances administered to a body, which often rely on a combination of two different imaging techniques. Examples are combinations of SPECT with CT and PET with CT, which both allow for quantitative measurements of radiation, however both only post-therapeutical and not during therapy.

U.S. Pat. No. 5,844,241 A proposes a combination of planar imaging and computer tomography (CT) data for dosimetry purposes in radio immune therapy. U.S. Pat. No. 7,291,841 describes a wearable detector array for SPECT, PET, and Compton scatter imaging in nuclear medicine. In "Toward Simultaneous Real-Time Fluoroscopic and Nuclear Imaging in the Intervention Room" by C. Beijst et al., Radiology, p. 142749, June 2015, a fusion of fluoroscopy and nuclear imaging is described.

The known techniques leave room for improvement in that they typically either do not allow measurement during therapy, lack near-real-time-characteristics, and/or have to compromise between spatial resolution and the ability for delivering the required information in near real time. Generally, there is also room for improvement with respect to the delivered spatial resolution and achievable precision of the delivered data.

In view of the above and for other reasons, there is a need for the present invention.

SUMMARY OF THE INVENTION

In light of the above, there is provided a method for determining a dose in real time during therapy with a therapeutic substance, which comprises a therapeutic radionuclide or is radioactively labelled, by using a nuclear imaging system with a nuclear detector, according to claim 1. Further, a system for determining a dose during therapy with a therapeutic substance, which comprises a therapeutic radionuclide or is radioactively labelled, is provided according to claim 10.

According to a first embodiment, a method for determining a dose in real time during therapy with a therapeutic substance, which comprises a therapeutic radionuclide or is radioactively labelled, by using a nuclear imaging system with a nuclear detector, is provided. The method comprises: providing a 3D image comprising at least a region of a body to be treated; identifying, in the 3D image, at least one target area to be treated, and defining a region of interest which includes the at least one target area; registering the position of a nuclear detector with regard to the 3D image; positioning the nuclear detector to detect radiation from a region of interest to which the therapeutic substance has been applied, and detecting radiation; quantifying in real time an actual target dose present in the target area, by evaluating the detected radiation; outputting information about the actual target dose; wherein the quantifying includes taking into account at least one of: previous simulations with known radiation distributions, previous measurements on known radiation distributions, and the radiation of a reference radiation source.

According to a further embodiment, a system for determining a dose during therapy with a therapeutic substance, which comprises a therapeutic radionuclide or is radioactively labelled, is provided. The system comprises a nuclear imaging system, comprising a nuclear detector and a control system, comprising a module for registering the nuclear detector with respect to a provided 3D image of a region of the body; a dose evaluation module for quantifying an actual target dose in a target area to be treated, by evaluating data from the nuclear detector; wherein quantifying in real time comprises taking into account at least one of: previous simulations with known radiation distributions, previous measurements on known radiation distributions, and the detected radiation of a reference radiation source.

Thereby, the above systems and methods can be integrated in a therapeutic workflow with no or minimal extra time and no or minimal extra effort and skills required for the interventional radiologist. The options and flexibility for dose planning and execution monitoring during therapy are significantly enhanced and improved. For an oncologist or radiotherapist, the treatment process is more transparent and the outcome of the treatment can be planned more effectively.

Further features, aspects, and details which can be combined with embodiments described herein are disclosed in the dependent claims, the description and the drawings.

BRIEF DESCRIPTION OF THE FIGURES

So that the above features can be better understood in detail, a more specific description is given with reference to embodiments of the invention. The appended drawings relate to embodiments of the invention and will be described shortly in the following.

DETAILED DESCRIPTION

Figure 1:
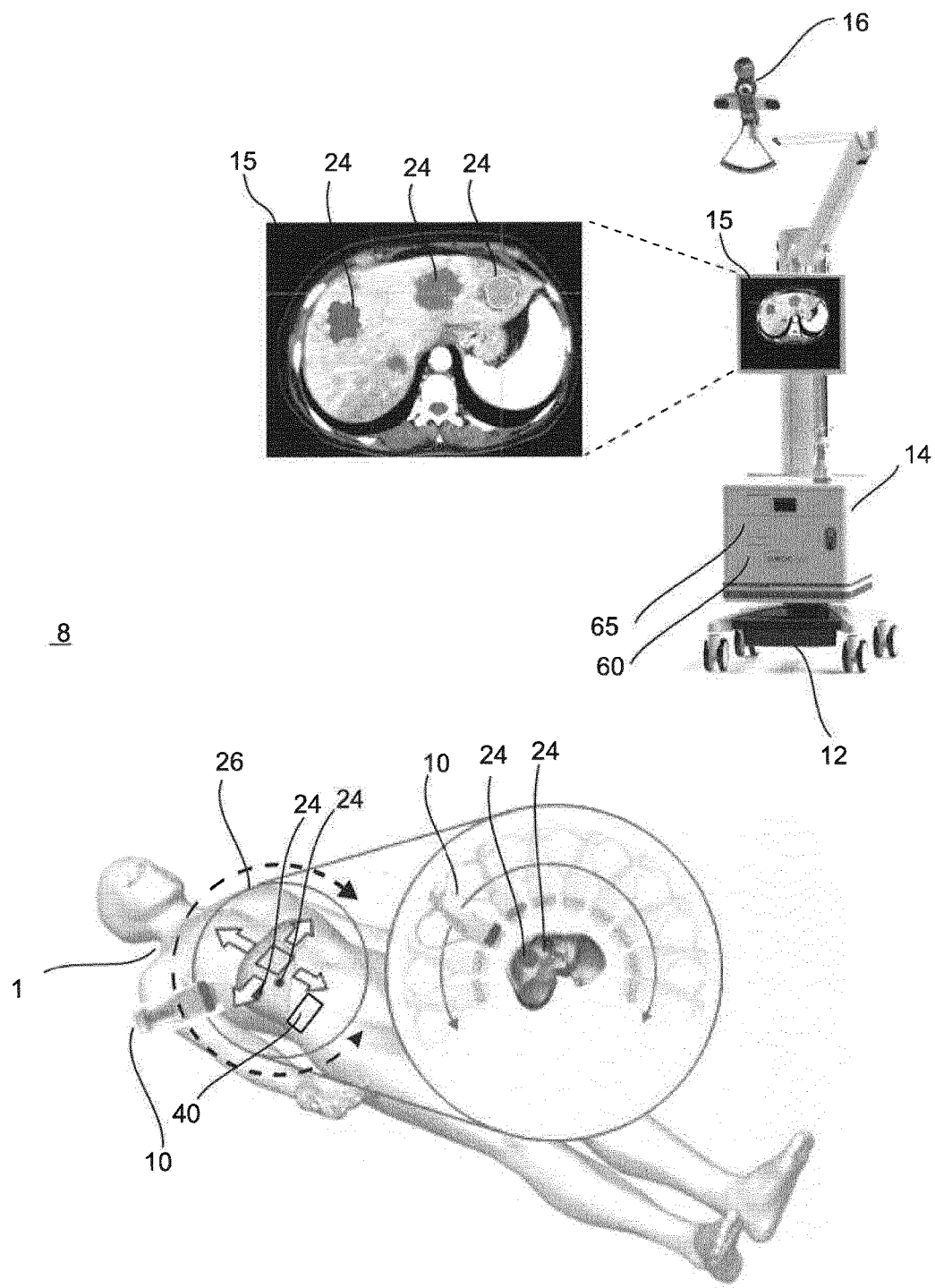
FIG. 1 shows a schematic arrangement of a system according to embodiments of the invention, together with the body of a patient.

In the following detailed reference is made to various embodiments of the invention, of which some are exemplarily illustrated by the drawings. Each example is provided by means of explanation and for a better understanding of the invention and shall not be construed as limiting the invention. Thus, features which are described with respect to one embodiment, or are being illustrated with respect to one embodiment, can be combined with other embodiments to generate further embodiments. It is intended that such modifications and variations are encompassed.

Within the following description and in the drawings the same reference signs relate to the same or similar components. Generally, only the differences between individual embodiments are explicitly described.

The expression "detection period" used herein denotes a period between the beginning of a first detection process and the end of last detection process. The first and last detection process can be identical such that the detection period is a period during which a detection process continuously takes place. The first and last detection can also be different. In a detection period other processes can therefore lie. For example, such other processes can be data evaluation processes. The at least one detection process taking place in the detection period is carried out by the same detector, respectively detector system, on the same object.

Specifying that an action is carried out "during a detection period" (or more generally during any period) is not to be construed in the sense that the action needs to fill the full period. The action can also only take place during part of the detection period. The action can also be interrupted.

The expression "freely movable" is generally understood in that the position and/or orientation of an object which is freely movable can be changed substantially arbitrarily. For example, a detector which is handheld is a freely movable detector. Also, a detector which is mounted to a robot arm with sufficiently many degrees of freedom is freely movable, wherein the robot arm is for example controlled by a user. A detector which is movable along a rail is movable but not freely movable.

The expression "continuous" includes, when relating to an action such as "continuously collecting detector data", an ongoing or regularly repeated action. The temporal distances between the regular repetitions can in principally in principal be arbitrarily short, i.e. quasi-continuous. However, it is obvious for the skilled person that, for example, physical constraints can limit arbitrarily short distances. For example, detectors can have so-called "dead times" such that during such dead times no detection can take place. Consequently, also during e.g. a continuous collection of the detector data, a regular repetition of data collection within the collection process may not be possible within time intervals that are shorter than said dead times. The notion "continuous" includes, when used in relation to an action, also the repetition or the iterated repetition in arbitrarily short time intervals. Also arbitrarily selected time intervals can, in principle, be arbitrarily shortly following each other, and limitations as explained above apply analogously.

The "generation of an image" includes the generation of image data without the need for output of such image data to an output unit, for example a monitor.

The term "target area", as used herein, is intended to mean an area of the body to which an administered therapeutic substance, or radiation dose, shall be delivered or is aimed at. Typically, the target area may be a lesion in an organ, such as a tumor.

As used herein, the term "actual target activity" or "target activity" is intended to be a quantitative measure for the number of decays per second (Becquerel) happening in the target area, as defined above, due to the radioactive decay of a radionuclide comprised in a therapeutic substance present in the target area. It has the unit 1/s. The actual target activity can be recalculated, when taking into account the decay rate of the radioactive material (radionuclide) which decays, to the number of atoms and thus the mass of the radionuclide which is present in the target area. It is thus also a proportional measure for the amount of therapeutic substance which has been deposited in the target area, e.g. in a tumor. The actual target activity is evidently and naturally smaller than the "applied radiation activity" or "injected activity", which is intended to mean the activity of the complete amount of the therapeutic substance applied to a body during a treatment (session) via a syringe or a catheter, as a fraction of the applied substance typically does not reach the target area for various reasons.

As used herein, the term "actual target dose" is intended to mean a division of the actual target activity, as defined above, by the mass of the body material (tissue, Bones, etc) comprised by the target area. It is measured in Becquerel per kg (of body mass). In radiotherapy, it is typically aimed at administering such an amount of therapeutic substance, that a certain predefined value of an actual target dose is met. The actual target dose is one of the key parameters to be monitored and controlled in embodiments described herein.

The term "region of interest" is a region of the body which includes the at least one target area. A region of interest may also comprise more than one target area, if present, or it may be identical to the target area(s). The region of interest is used herein in the sense that it may be of interest not only which amount or dose of a therapeutic substance has accumulated in the target area to be treated, but also which amount has accumulated in the body tissue surrounding the target area, or in more remote regions. The region of interest is typically, but not necessarily, identical to a region of the body which is in the field of view of a nuclear detector during data acquisition. In an example, the region of interest may be the liver and neighboring abdominal regions during a therapeutic treatment of a tumor (the target area) in the liver.

As used herein, "a region of a/the body to be treated" includes at least the region of interest and the target area(s). It may be defined with respect to a 3D image, which can typically be CT, MRT, ultrasound, or other, and may for example comprise the complete abdominal region when the target area is in the liver. When the target area is, in another non-limiting example, in the brain, the region of the body to be treated would be the entire head and, optionally, neck region.

As used herein, the term "Selective internal radiation therapy" or "SIRT" is intended to mean a form of radiation therapy used in interventional radiology to treat tumors. The treatment involves injecting microspheres, comprising or consisting of radioactive material, into the arteries that supply the tumor. As malignancies (including primary and metastatic liver cancers) are often hypervascular, tumor blood supplies are often increased compared to those of normal tissue. In a non-limiting example used throughout this disclosure, the organ to be treated is the liver. The liver has a dual blood supply, receiving blood from both the hepatic artery and the portal vein. Hepatic malignancies derive most of their blood supply from the hepatic artery; whereas the normal liver derives most of its blood supply from the portal vein. Therefore, delivery of radioembolic particles through the branch of the hepatic artery supplying a tumor will preferentially lead to deposition of the particles in the tumor, while sparing normal liver from harmful side effects. Thereby, the microspheres are typically dimensioned such that they accumulate in smaller blood vessels leading to embolism of the microspheres in a certain area in the border region of the tumor, where the blood vessels have an average size which promotes the embolism and blocks their further movement. Hence, it is important to monitor that the microspheres are injected into an artery close to and leading to the tumor, which is typically carried out by inserting a catheter and positioning its end such that the microspheres will flow to the aimed region of the organ to be treated, such as the liver.

This process is typically carried out under real time monitoring using angiography of the blood vessels. Once the catheter is correctly positioned, the microspheres are injected from an outside reservoir through the catheter. The amount of activity administered to the body (applied radiation activity or injected activity) is thereby directly correlated to the number of microspheres each transporting a certain amount of radionuclide. It is obvious that it is relevant from a medical point of view to be able to control which fraction of the injected microspheres have actually reached the tumor tissue or, more general, lesion (henceforth also called target area), and which fraction is deposited outside the tumor in other areas of the organ to be treated, in areas adjacent to the organ, or which fraction is transported in the blood stream away from the target area. The latter is, e.g., of particular interest for a liver treatment, as there exists a lung shunt which may lead to a flow of a fraction of the injected microspheres with the bloodstream to the lung, which is highly undesirable.

Generally, embodiments described herein pertain to a method for determining a dose in real time during therapy with a therapeutic substance. The latter typically comprises a therapeutic radionuclide or is a non-radioactive therapeutic substance which is radioactively labelled with a radionuclide. Generally, a nuclear imaging system with at least one nuclear detector is used, wherein imaging does not necessarily mean that an optical image is provided, but that concentrations of therapeutic substances are provided as 3D data, wherein representations of this data may typically also be displayed on a computer screen. For obtaining anatomical information about the target area and the region of interest, typically a pre-interventional 3D image is employed, which comprises at least the region of the body to be treated. The pre-interventional 3D image, henceforth called 3D image, may typically be a CT, MRT, ultrasound, or other image having suitable spatial resolution and contrast to identify therein the target area(s) to be treated. The 3D image may be produced some time prior to the therapy, however the image data will be most accurate with only a small delay, such as some hours, between image generation and therapy.

In all detailed examples of embodiments herein, except when stated differently, it is assumed as a non-limiting example that the provided 3D image is a pre-interventional CT 3D image. Further, it is generally assumed, also as a non-limiting example, that the applied treatment is a radiotherapeutic treatment of at least one lesion in the liver, which is exemplarily a tumor.

In embodiments, the 3D image is initially segmented. Thereby, the approach for the segmentation may, e.g., include rule-based systems, level-set frameworks, learning models of the shape and appearance of objects from training data and fitting these models to unseen data, elastic registration through atlas matching, and classification techniques from pattern recognition and machine learning, or other. Currently, an algorithm using publicly available methodology is the two-stage semi-automatic organ segmentation framework using radial basis functions and level sets, as disclosed by Andreas Wimmer, Grzegorz Soza and Joachim Hornegger.

The result is a pre-interventional, annotated 3D image. In the annotated 3D image, a tracking target is identified or defined. This tracking target is then registered to another, optically tracked target, which may for example be at least one physical marker on the body surface of the patient. Any nuclear detector data, including typically the pose of the detector(s), has to be registered with the 3D image in order to be able to identify the spatial relation between the body in the 3D image and the radiation received by the nuclear detector. This process is known in the art and is henceforth called "CT registration".

In the 3D image, a region of interest is defined, which includes the at least one target area to be treated. The position of a nuclear detector is then registered with regard to the 3D image. The nuclear detector is positioned in a calculated position, where it may in embodiments reside during the detection process, or it is moved—via, e.g., a robot arm, or manually—along a calculated trajectory. During the radiation detection, the detector detects radiation from the region of interest to which the therapeutic substance has been applied. On the basis of the detected data set collected over a defined time span, the activity due to therapeutic substance is quantified for the region of interest by a dose evaluation module in a control module of the system.

The deposited target dose is calculated for different subregions in the region of interest. The size of the subregions is determined by the defined spatial resolution of the system, or can be manually defined. Typically, the region of interest is segmented into a plurality of voxels. Each voxel may be a cube with a dimension of a few millimeters, for example 2 mm to 10 mm. The smaller the voxels are, the larger is the resolution of the system, and the more detailed is also the obtained information on the dose distribution in the region of interest and the target area. The actual target dose, expressed as a deposited activity of the therapeutic substance per mass unit of the target, is derived from the detected data in conjunction with additional information. This additional information may include previous simulations with known radiation distributions on the basis of the 3D image, previous measurements on known radiation distributions on a physical phantom (body phantom), and the radiation of a reference radiation source which is placed in the detection area during data acquisition.

FIG. 1 shows a system 8 for determining a dose during therapy with a therapeutic substance 5 (not shown), which comprises a therapeutic radionuclide or is radioactively labelled, according to embodiments of the invention. The system comprises a nuclear imaging system 12. The latter comprises a nuclear detector 10 and a control unit 14. The control unit comprises a registration module 60 for registering the data delivered by the nuclear detector 10 with respect to a provided, annotated 3D image 15. The annotated 3D image comprises at least a region of a body to be treated 22 with the target area(s) 24. In the non-limiting example of FIG. 1, three target areas 24 (lesions) are shown. The nuclear detector 10 is typically tracked by a tracking unit 16 operably connected to the control unit 14. In embodiments, the tracking can be an optical, electromagnetic, mechanical, robot-based, radio wave-based, sound wave-based, goniometer-based, potentiometer-based, gyroscope-based, acceleration sensor-based, radiation-based, or x-ray-based detection unit, or an infrared or white light detection unit or another kind of detection or tracking unit 16.

A dose evaluation module 65 serves for quantifying the actual target dose in a target area 24 to be treated, by evaluating data delivered by the nuclear detector 10. For the quantification, the detector data is evaluated on the basis of standard procedures of 3D SPECT imaging which is known in the art. 3D SPECT imaging is suitable to deliver sufficient spatial resolution and contrast for the intended purpose, however a 3D SPECT image of a radiation distribution is not suitable for providing reliable information about the absolute radiation in a voxel, or in a volume of interest made up of a plurality of voxels. This is accounted for in embodiments in that a reference source 40 with a known and isotropic radiation intensity is placed adjacent to the target area 24 on, or close to, a body surface. During the radiation detection by the nuclear detector 10, the detector thus does detect radiation emitted from a therapeutic substance administered to the body and also the radiation from the known reference source 40. The dose evaluation unit 60 may thus compare the intensity of the reference source 40 to the detected data from the target area(s) 24 and can thus calculate the absolute intensity of the radiation in the target area(s) 24.

The nuclear detector 10 may in these embodiments comprise a Gamma camera 11 or a Gamma probe 10a. The detector may be integrated in a gantry, be a freely movable handheld detector or be mounted to a robotic arm. In other embodiments described herein, the nuclear detector may be a grid 13 of nuclear detectors/Gamma probes.

Figure 2:
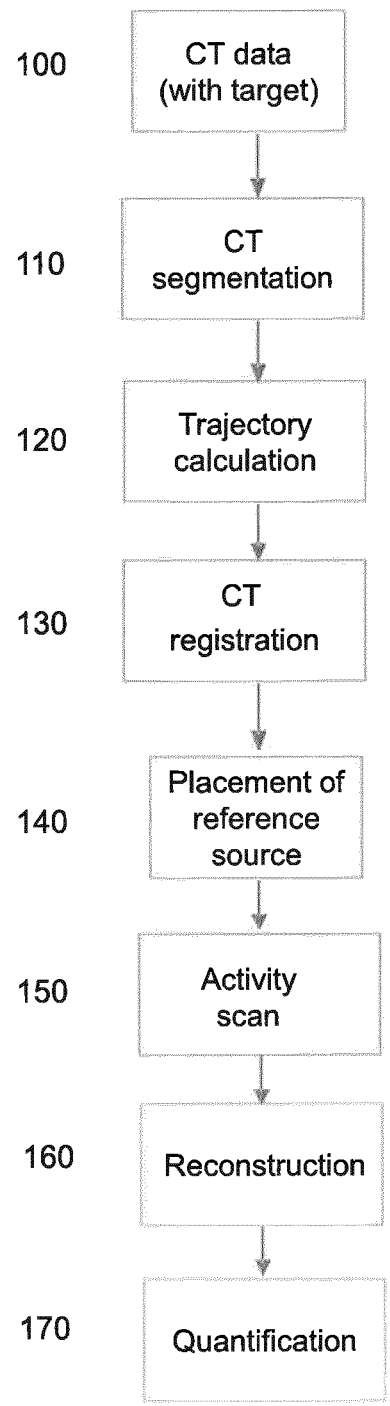
FIG. 2 schematically shows a method according to embodiments of the invention.

In FIG. 2, a method for determining a dose in real time during therapy with a therapeutic substance 5 is schematically depicted. As was previously described, CT data provided as a 3D image, which includes the target area 24, is provided in a block 100. The CT data undergoes a segmentation as previously described in a block 110, and becomes annotated 3D image 15. From the segmentation, which may be designed to be carried out semi-automatically, automatically or manually, and to require the input of a radiologist or oncologist in the process for precisely identifying the target area(s) 24 to be treated, information about the location of the target area(s) 24 in the body 1 is derived. Further, when the location of the target area(s) 24 has been determined, a starting position of the nuclear detector 10, and a trajectory for its movement in order to obtain reliable data about the radiation distribution in the region of interest 26 is calculated in a block 120. To this end, a planning algorithm is provided in the control unit 14. The data delivered from the nuclear detector 10 is then registered with the CT image data in a block 130. The reference source 40 is, if not already in place, placed on the body surface or adjacent to the body 1 in a block 120, so that it is in the region of interest 26 at a location which is in the field of view of the nuclear detector 10 during its planned path about the trajectory. The control unit 12 of the nuclear imaging system 12 may comprise an algorithm to assist in the suitable placement of the reference source 40. Thereby, the radionuclide comprised in the reference source 40 typically has a half-life of greater than 5 minutes, more typically greater than 10 minutes. Its gamma energy is typically in a range which is detectable by the employed gamma detector, such as from about 20 keV to about 350 keV. Examples for suitable radionuclides are Co-57, Tc-99m, or Gd-153.

As depicted in FIG. 2, in a block 150 the activity scan with the nuclear detector 10 is carried out. The scan typically starts shortly before or during the administration/injection of the therapeutic substance 5 to the body 1. In this non-limiting example, the therapy is based on Selective Internal Radiation Therapy (SIRT), as described above, while the target area is a tumor in the liver. Prior to the activity scan 150 and the injection of the therapeutic substance 5 in the form of Y-90 comprising microspheres, an angiogram is performed to identify the branch of the hepatic artery supplying the tumor, that is the target area 24. The tip of a catheter (not shown) is selectively placed within the artery, and the Y-90 microspheres are infused. The delivery of the microspheres through the branch of the hepatic artery supplying a tumor will preferentially lead to deposition of the particles in the tumor due to the embolic effect promoted by the choice of the size of the microspheres, while sparing healthy liver tissue from harmful side effects. The therapeutic methods per se as described herein are included only for explaining embodiments, for reference and as examples.

During the activity scan 150, the nuclear detector 10 may be held and moved by an operator, wherein instructions for movement may be signaled optically or acoustically via the control unit 14. Also, the nuclear detector 10 may be moved by a robot arm (not shown), the movement of which is controlled by the control unit 14 according to the planned trajectory and speed of movement. The nuclear detector 10 is typically tracked by a tracking unit 16 (see FIG. 1). In embodiments, the tracking can be an optical, electromagnetic, mechanical, robot-based, radio wave-based, sound wave-based, goniometer-based, potentiometer-based, gyroscope-based, acceleration sensor-based, radiation-based, or x-ray-based detection unit, or an infrared or white light detection unit or another kind of detection or tracking unit. The nuclear detector 10 is typically configured to detect Bremsstrahlung caused, for example, by Y-90 beta radiation from the microspheres in the surrounding tissue. Therefore, the control unit may be configured to detect, in an example, in an energy window from about 100 keV to about 160 keV, but also other energy windows are possible for Y-90, as known to the skilled person. In other examples with different radionuclides, the energy window(s) may be selected to encompass peak energies at 173 keV and 247 keV with a respective tolerance of +/−10 percent, for example, for In-111. For Ga-67, suitable energy peaks are at 94 keV, 184 keV, 296 keV and 393 keV, also with +/−10 percent.

After the activity scan, the control unit 14 calculates a nuclear image on the basis of the detected radiation from the nuclear detector 10. The image reconstruction is carried out similar to SPECT imaging, which is well known in the art, in a reconstruction step in a block 160. For the detailed procedure of the image reconstruction, it is referred to Byrne, C., "Likelihood maximization for list-mode emission tomographic image reconstruction," in IEEE Transactions on Medical Imaging, vol. 20, no. 10, pp. 1084-1092, October 2001, doi: 10.1109/42.959305, in conjunction with Harrison H. Barrett, Timothy White, and Lucas C. Parra, "List-mode likelihood," J. Opt. Soc. Am. A 14, 2914-2923 (1997).

At the same time of the detection of the Bremsstrahlung from the region of interest, also the radiation from the reference source 40 is detected. The detected radiation from the reference source is used, as a source with known intensity, for evaluating the deposited activity (actual target activity/actual target dose) in the target area 24 in the form of the Y-90 microspheres by the dose evaluation module 60 in the control unit 14. In a quantification step 170, the control unit 14 calculates the accumulated activity and dose in the target area 24, and optionally for other regions, too. The activity and dose is typically calculated for each voxel in the target area, and also in the rest of the region of interest.

By summing up the activity for the voxels attributed to belong to the target area(s) 24 on the basis of the annotated 3D image 15, the value of actual target activity and actual target dose deposited in the target area 24 is calculated. Also, the activity and dose for voxels of the respective organ not belonging to the target area can be calculated on the basis of the detector data. As the injected activity, which has been injected into the body 1 at a certain point in time, is typically known due to the monitoring of the application mechanism, the control unit typically calculates and displays the activity/dose deposited in the tumor/target area, the activity/dose which is deposited in areas of the body 1 other than the target area 24 (the tumor), but in the region of interest covered by the field of view of the nuclear detector 10. When the activity values for the target area(s) 24 and the region of interest 26 are subtracted from the injected activity, a portion of the injected activity having left the region of interest (e.g., via the blood stream, such as the lung shunt) may be calculated. If the difference between the injected activity and the actual target activity calculated to be deposited in the target area 24, and/or in the whole region of interest 26, exceeds a certain threshold, this may be signaled by the control unit 14 to an operator. It can also be determined if the actual target dose has reached at least one of: a predefined upper threshold $S_U$, and a predefined lower threshold $S_L$. Also, a threshold for an activity not deposited in the region of interest may be previously defined and watched by the control unit 14. In this manner, it can be supervised if the activity leaving the liver via the lung shunt becomes too high, so that a signal is provided for an operator. This may lead to a renewed placement of the catheter, for example, or at least to a check of its position via angiography.

The above methods may for example be used to perform an administration of the therapeutic substance as fractions and in intervals. A predefined time-span after administering, for example, 10 percent or 20 percent of the pre-planned activity as the injected activity, hence the respective fraction of the therapeutic substance 5 comprising the microspheres, the monitoring according to the above method is performed. After about 10 seconds to 5 minutes, the system displays the results of the determined activity/dose distribution on the screen of the control unit 14. Further, the quantitative values for the activities/doses for the different fractions may be displayed as numbers, together with various relations/parameters of choice, for example the ratio between the determined actual target activity in the target area 24 and the rest of the injected activity. If the ratio is regarded to be within predefined limits, the operator may administer the next fraction—of 10 to 30 percent—of the pre-planned activity. Subsequently, another determination of the parameters is carried out by performing the activity scan 150, followed by a further (final) injection, if the parameters are regarded to be sound by an operator.

Figure 7:
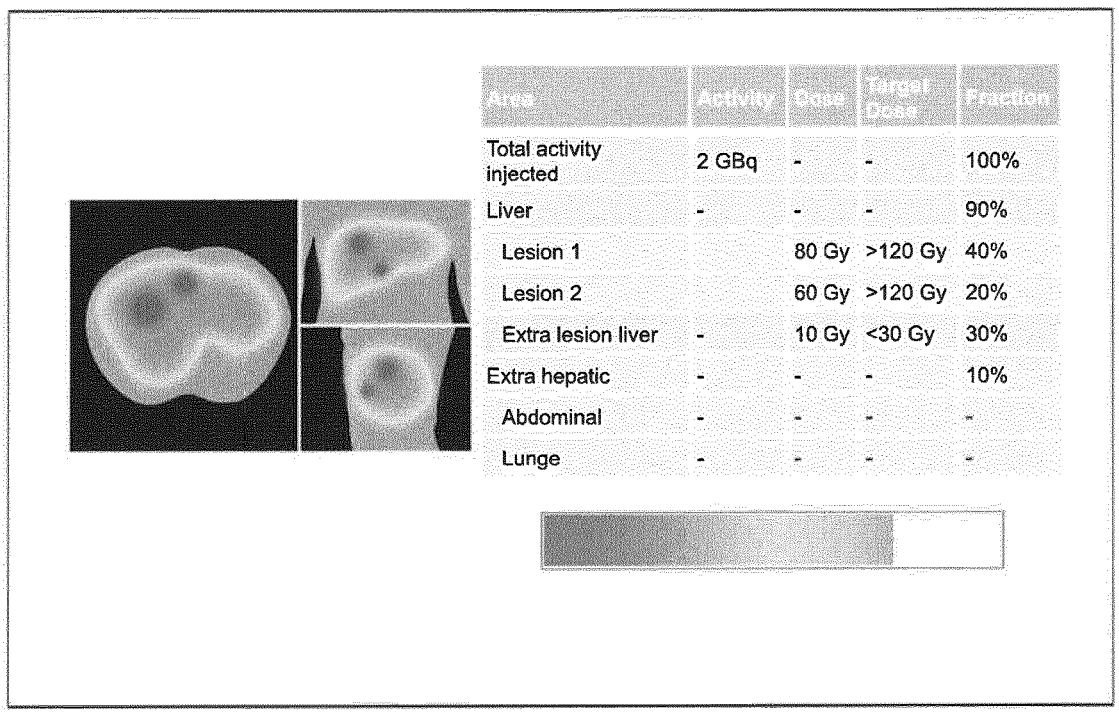
FIG. 7 shows an exemplary screen output of a system according to embodiments.

As an example, the treatment of a tumor in the liver is monitored as described above. By the disclosed method, a qualitative method is provided to visualize the quantitative distribution of an administered therapeutic substance in lesion(s), in the extra-lesion liver, in an extra hepatic abdominal region, and the lung, in real time or near real time. Thereby, a respective quantitative measurement and calculation is suitable to provide the extra hepatic abdominal uptake, the lung uptake or lung shunt fraction, the healthy liver uptake, and the lesion uptake. An exemplary screen output on the screen of the control unit 14 is shown in FIG. 7. Further, a ratio between healthy liver and lesion uptake may be calculated and dynamically imaged to show an embolization effect.

Figure 3:
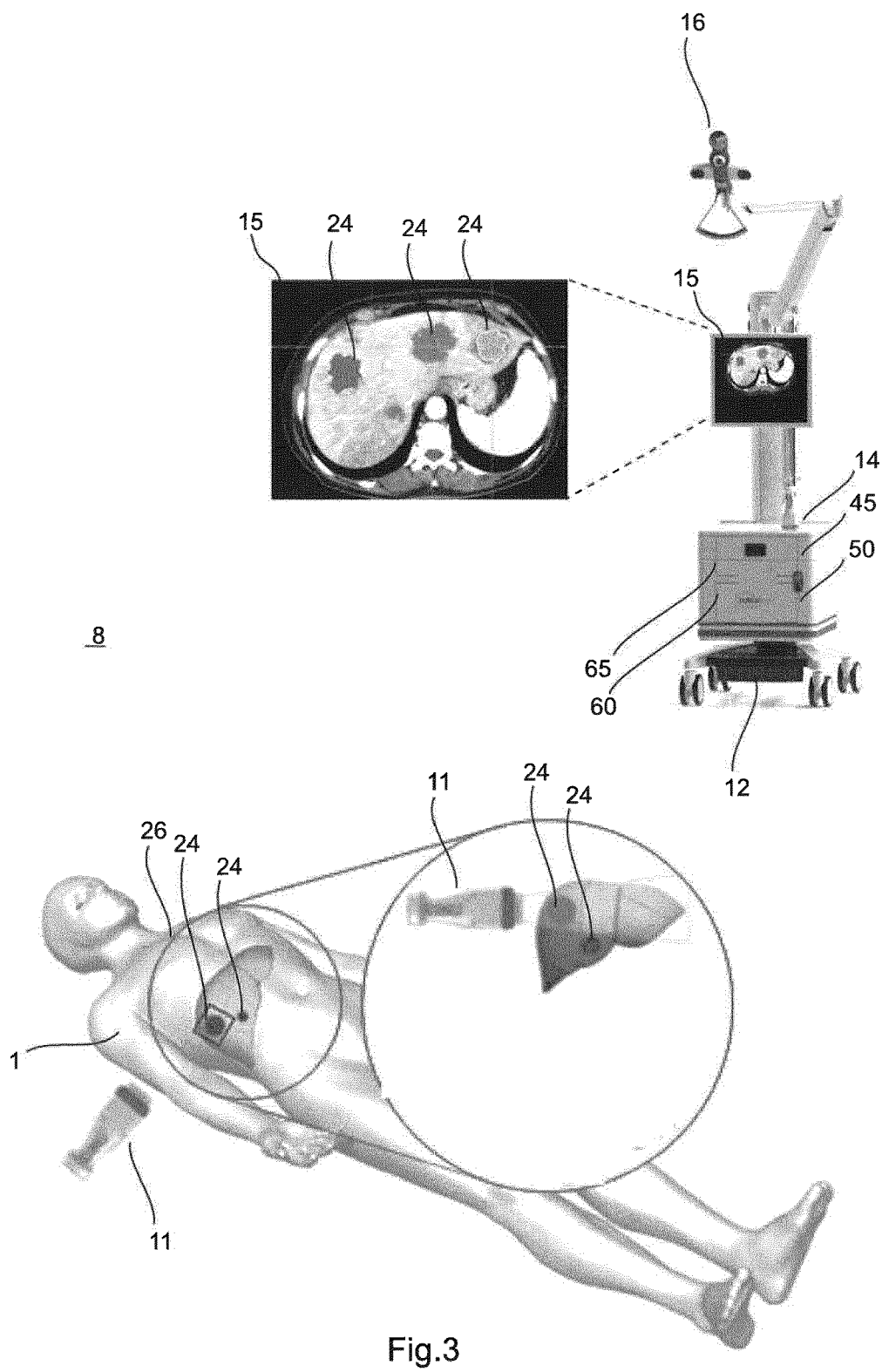
FIG. 3 shows a schematic arrangement of a system according to further embodiments of the invention, together with the body of a patient.

In FIG. 3, a further embodiment of the invention is shown, which bears significant differences with respect to the embodiment of FIGS. 1 and 2. Predominantly, the nuclear detector 10 of system 12, which moves along a trajectory in the embodiment of FIGS. 1 and 2 during radiation detection, is kept stationary in FIG. 3. It is typically a 2D Gamma camera 11 having a resolution of from at least about 16 by 16 pixels up to about 512 by 512 pixels, or more. The Gamma camera 11 is tracked by a tracking unit 16 operably connected to the control unit 14, wherein the tracking has the function of enabling the registration between the data from the Gamma camera 11 and the annotated 3D image 15. The nuclear imaging system 12 further has additional features comprised in the control unit 14, namely pre-calculated simulations of detection values for a plurality of radiation distributions which are provided in a first database 45 in the control unit 14. The simulations in the database 45 are compared with the detected radiation in order to have an additional basis for a probability calculation for determining the radiation distribution in the region of interest, described further below as (deep) learning.

Figure 4:
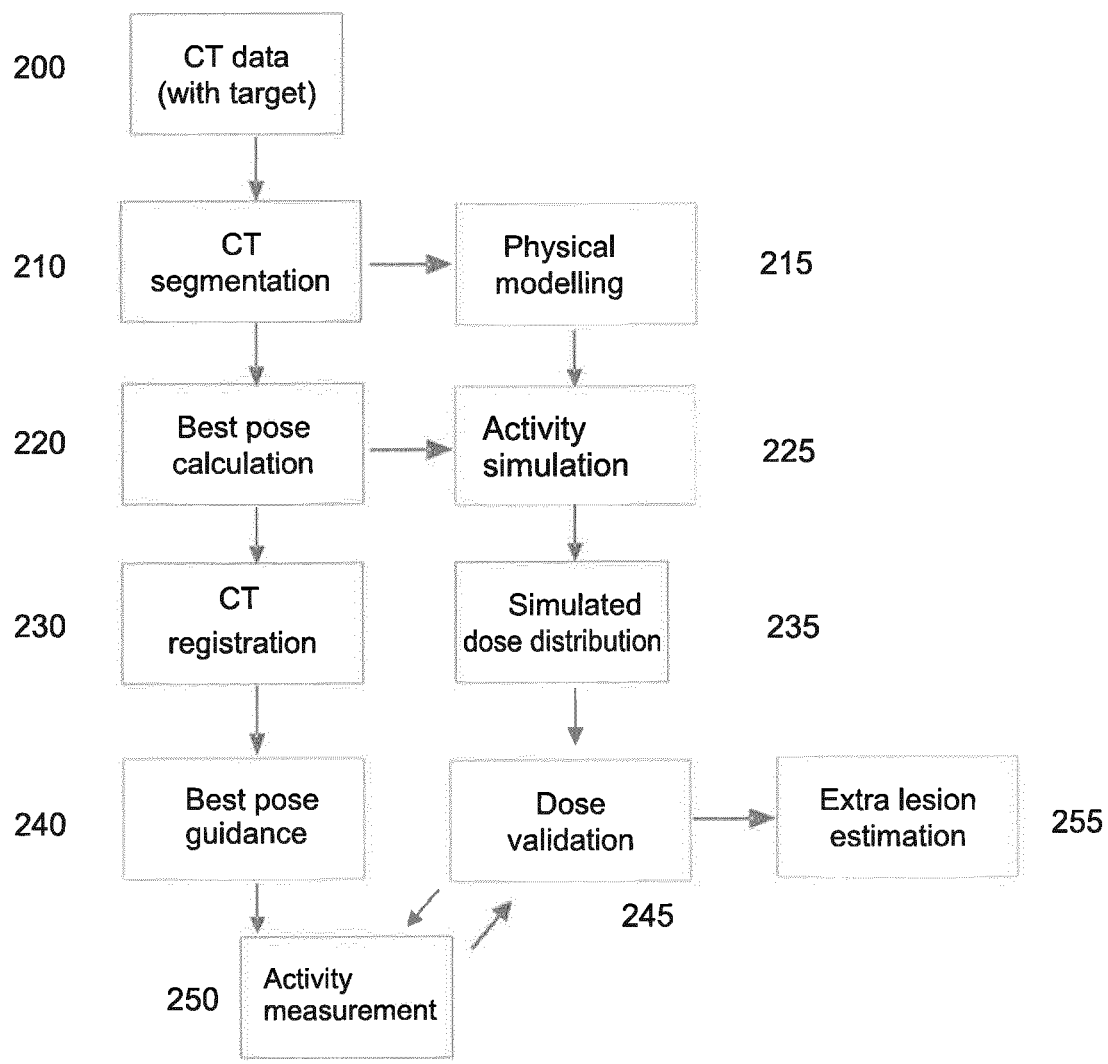
FIG. 4 schematically shows a method according to further embodiments of the invention.

The pre-calculated simulations are typically calculated prior to the treatment on the basis of the annotated CT image 15, wherein the position and shape of the lesion(s) are determined in the annotated CT image 15, shown schematically in FIG. 4 as a block 210 "CT segmentation", derived from previously provided CT data/CT image (block 200). For the simulations, the tissue types and bones are identified and taken into account with their differing absorption and scattering behavior, in a block 215 "Physical Modelling", with respect to the (later) measured range of Bremsstrahlung and gamma radiation during actual measurement on a patient during treatment. Based on these parameters, scenarios are produced concerning different distributions of a given injected activity over the identified lesion(s) (which is/are defined as the target area 24) and other body tissue, wherein the simulations are calculated for dedicated, predefined detector positions, based on the position of the lesions and different tissue/bone types determined in step 210 from the annotated CT image 15. The detector positions, or more precisely detector poses, employed in this "Activity Simulation" (block 225 in FIG. 4), are determined beforehand in a "Best pose calculation" in a block 220. Emitted Bremsstrahlung and gamma radiation, which will be detected by the hypothetical Gamma camera at the determined best pose detector positions, are simulated by the control unit 14. The different simulated scenarios comprise the respective pose of the Gamma camera, data about the simulated radiation distributions, and are stored in the first database together with the simulated response of the Gamma camera for each individual simulated radiation distribution and the respective position of the Gamma camera, in a block 235. This first database 45 may be coupled to a (deep)

learning algorithm implemented in the control unit 14. During the actual measurement during treatment, real live data from the Gamma camera 11 and the precalculated radiation distributions are used to incrementally and continuously decide on a best fitting scenario in a "Dose validation" step in block 245.

Further, the control unit 14 may comprise a second database 50, refer to FIG. 3. It comprises radiation detection values for a variety of nuclear radiation distributions in a physical body phantom. These measurements have previously been carried out and been stored together with the known test radiation distributions. These scenarios in the second database 50 can also be used as input for the computation of the actual target dose in block 245 in FIG. 4. The body phantom may be, for example, a plastic cylinder filled with water, wherein some spheres filled with a radionuclide are positioned. The spheres may have a diameter from a few millimeters to several centimeters and represent the lesions/tumors. The lesions may, e.g., be placed to be virtually in a region where the liver is—or the organ or region to be mocked-up for the measurements—when the cylinder is representing a thorax. The different radiation distributions caused by the spheres are stored in the database 50 together with the simulated response of a Gamma camera used in these tests.

Expressed differently, data from a nuclear detector based on known radiation distributions are stored in the database together with the radiation distributions and the pose of the detector. The data from the nuclear detector may thereby be the result of previously calculated simulations (first database 45) or from previously carried out measurements on phantoms (second database 50). During the actual measurement, live data from the detector is continuously compared to the stored detector data from the databases 45, 50. From this comparison, the most probable radiation distribution is derived, while the process is constantly repeated using updated live detector data. Thereby, an employed (deep) learning algorithm may be based on an autoencoder, comprising an encoder and a decoder, which is a known paradigm. The encoder uses raw data, which in this embodiment the 2D image from the Gamma camera 11, as input and produces features or representation as output. The decoder uses the extracted feature from the encoder as input and reconstructs the original input raw data as output. Thereby, the output is the radiation distribution in the region of interest 26 comprising the target area 24. Thereby, the output is constantly updated on the basis of the live data from the Gamma camera 11.

Hence, according to embodiments described with respect to FIG. 3 and FIG. 4 above, the administration of a radiation dose to a body can be monitored similarly as described with respect to FIG. 1 and FIG. 2. That is, the administration of the therapeutic substance is typically administered as fractions and in intervals. A predefined time-span after administering, for example, 10 percent or 20 percent of the pre-planned activity as the injected activity, hence e.g. the respective fraction of the therapeutic substance comprising the microspheres, the monitoring according to the method of FIG. 4 is performed. After about 10 seconds to 5 minutes, the system displays the results of the determined activity/dose distribution on the screen of the control unit 14. Further, the quantitative values for the activities/doses for the different fractions may be displayed as numbers, together with various relations/parameters of choice, for example the ratio between the determined actual target activity in the target area 24 and the rest of the injected activity—which are determined during the Dose validation 245 and the Activity measurement 250 in FIG. 4. If this ratio is regarded to be within predefined limits, the operator may administer the next fraction—of, e.g., 10 to 30 percent—of the pre-planned activity. Subsequently, a further determination of the parameters is carried out, followed by a further (final) injection, if the parameters are regarded to be sound by an operator. Simultaneously, a dose which has been deposited in areas other than the target area 24 can be estimated in the "Extra lesion estimation" in block 255 in FIG. 4.

Figure 5:
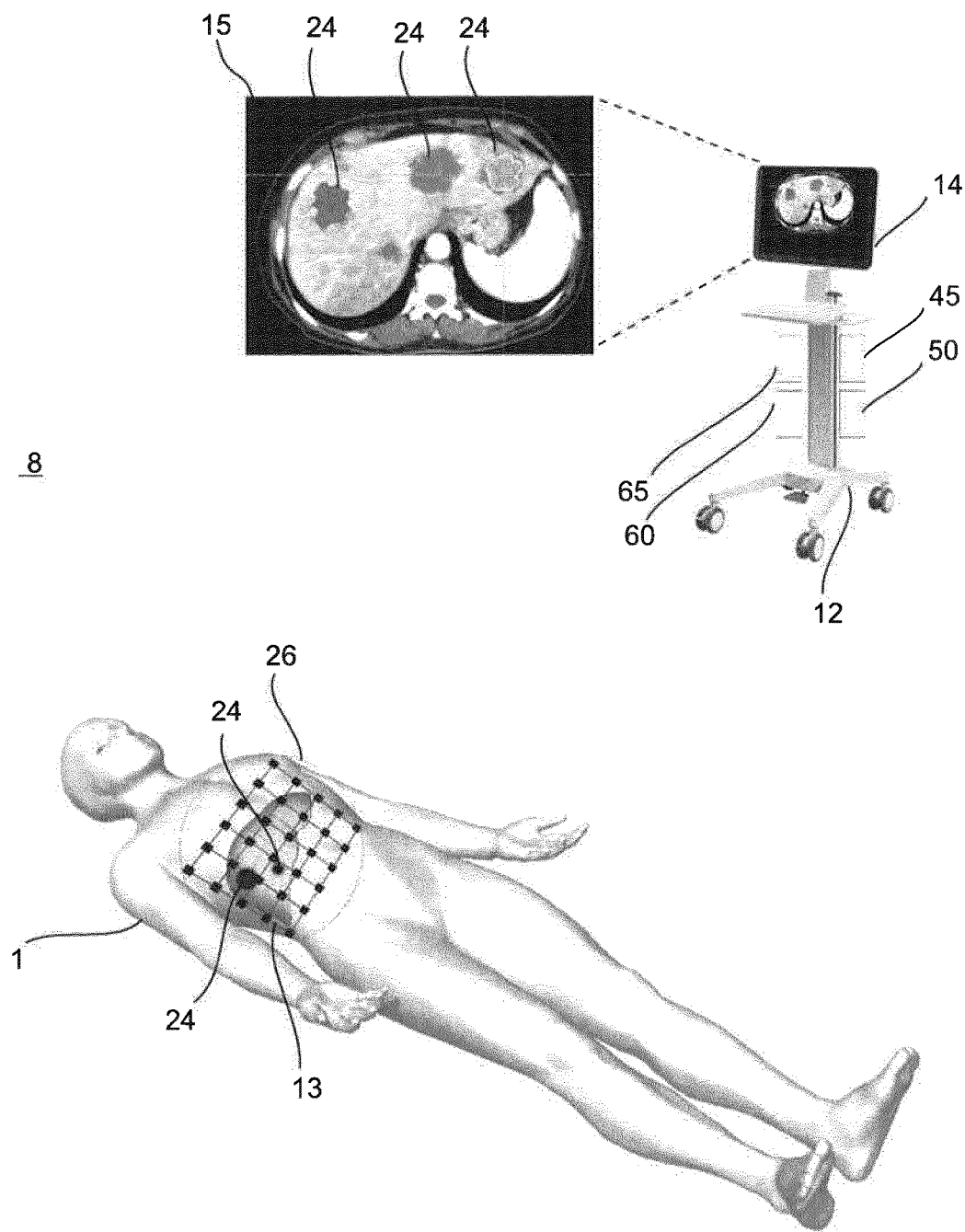
FIG. 5 shows a schematic arrangement of a system according to yet further embodiments of the invention, together with the body of a patient.

In FIG. 5, a further embodiment of the invention is schematically shown. Therein, differently from the embodiments shown in FIG. 1 and FIG. 2, the nuclear detector 10 comprises a grid of a plurality of single nuclear detectors/Gamma detectors. This grid 13 of Gamma detectors is typically arranged in a matrix structure and is positioned adjacent to a surface of the body 1. The grid 13 is typically positioned adjacent to the region of interest 26 comprising the target area 24, hence the lesion(s).

While in the embodiment of FIG. 1, the nuclear detector 10 has a relatively low resolution and is movable, and in FIG. 3 the nuclear detector is a Gamma camera 11 which is substantially stationary, in FIG. 5 the nuclear detector 10 in the form of grid 13 is comprised of a multitude of single Gamma detectors each having a low resolution, typically in the form of Gamma probes. The underlying concept is to derive the necessary spatial resolution through the grid 13 of detectors being located at different positions encompassing the area of interest 26 with the target area 24.

Similarly to the method described with respect to FIG. 4, a first database 45 with simulations and a second database 50 with previous test measurements are employed. Differently to the method of FIG. 4 pertaining to the use of the Gamma camera 11, when employing the grid 13, data stemming from the individual detectors of the grid 13 are compared with the stored data of the individual detectors—instead of comparing 2D images from a Gamma camera 11 with stored images. Further, a deep learning algorithm is employed which uses data from the first database 45 and/or the second database 50 as input or training data. During the actual measurement on the patient, the (deep) learning algorithm decides on which scenario from the database(s) fits best to the real time set of detector data from the grid 13.

Figure 6:
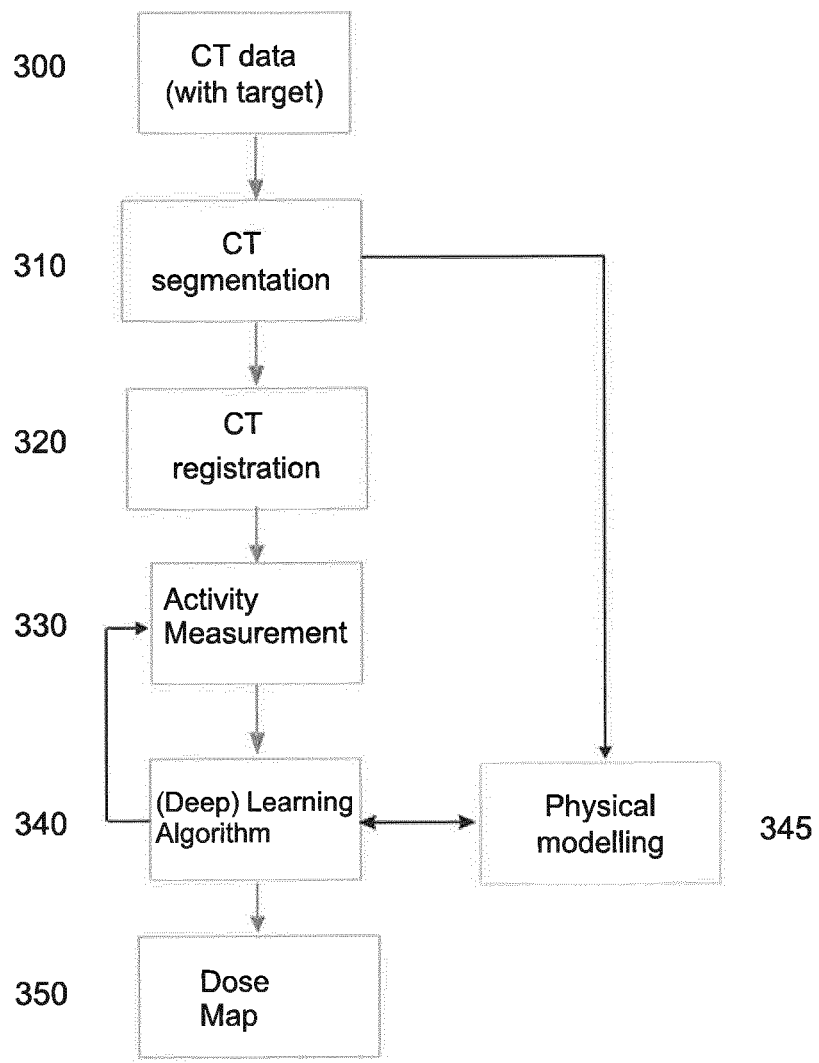
FIG. 6 schematically shows a method according to yet further embodiments of the invention.

In FIG. 6, the method when employing the system of FIG. 5 is schematically depicted. Thereby, the steps in blocks 300, 310, and 320 are essentially similar to those already described with respect to FIG. 2 and FIG. 4, also similar is the "Physical modelling" in block 345. The "Activity measurement" in block 330 is based on the output of the multitude of detectors of the grid 13. The "Deep learning algorithm" in block 340 was described above. Thereby, the deep learning algorithm may be based on an autoencoder, comprising an encoder and a decoder, which is a known paradigm. The encoder uses raw data, which in this embodiment are the spectra from the detectors of the grid 13, as input and produces a feature or a representation as output. The decoder uses the extracted feature from the encoder as input and reconstructs the original input raw data as output. Thereby, the output is the radiation distribution in the region of interest 26 comprising the target area 24. The output is constantly updated on the basis of the live data from the grid 13, similarly to the case of FIG. 3 and FIG. 4. The output in block 350 has the form of a dose map.

FIG. 7 shows a non-limiting example of an output screen of the control unit 14 during measurement, according to embodiments described herein.

With embodiments described herein, systems and methods are provided which enable an operator, such as an oncologist or radiotherapist, to monitor the parameters of, e.g., a SIRT treatment in near real time. That is, it can be determined which quantitative fraction of the amount of injected radiation (such as microspheres, or any other therapeutic substance comprising a radionuclide) has reached its target area, or several target areas if applicable, and the respective actual target dose per lesion—or per a part thereof—is calculated. At the same time, the activity or dose of radiation unintendedly deposited in surrounding tissue of the organ to be treated, and/or the activity/dose unintendedly deposited in other regions of the body may be quantitatively determined and even be localized, if desired. The same is valid for other methods of medical treatment where a therapeutic substance comprising a radionuclide is injected or inserted into the body and has to be monitored in order to control its distribution, such as, for example, in radio immune therapy.

While the forgoing is directed to embodiments of the invention, other and further embodiments of the invention can be devised without departing from the scope of the invention set forth in the following claims.

The invention claimed is:

1. Method for determining a dose in real time during therapy with a therapeutic substance, which comprises a therapeutic radionuclide or is radioactively labelled, by using a nuclear imaging system with a nuclear detector comprising:
   providing a 3D image comprising at least a region of a body to be treated;
   identifying, in the 3D image, at least one target area to be treated, and defining a region of interest which includes the at least one target area;
   registering the position of the nuclear detector with regard to the 3D image;
   positioning the nuclear detector to detect radiation from a region of interest to which the therapeutic substance has been applied, and detecting radiation;
   quantifying in real time an actual target dose present in the target area, by evaluating the detected radiation; and
   outputting information about the actual target dose;
   wherein the quantifying includes taking into account at least one of: previous simulations with known simulated radiation distributions, previous measurements on known radiation distributions, and the radiation of a reference radiation source.

2. The method of claim 1, further comprising:
   determining whether the actual target dose has reached at least one of: a predefined upper threshold $S_U$, and a predefined lower threshold $S_L$.

3. The method of claim 1, further comprising determining a difference d between the applied radiation activity and the actual target activity, and putting out a signal related to the difference, and/or if it has reached a predetermined threshold.

4. The method of claim 1, wherein the nuclear imaging system is adapted to detect Bremsstrahlung caused in the body by the therapeutic substance.

5. The method of claim 1, wherein the nuclear detector comprises:
   a. a 2D Gamma camera or a Gamma probe; or
   b. a grid of Gamma detectors, positioned adjacent to a surface of the body.

6. The method of claim 1, wherein pre-calculated simulations of detection values for a plurality of radiation distributions are provided in a first database, and wherein the actual target dose is calculated by comparing the simulations and the detected radiation.

7. The method of claim 1, wherein a second database comprises measured radiation detection values for a variety of nuclear radiation distributions in a physical body phantom, and wherein the content of the second database is used as input for a computation of the actual target dose.

8. The method of claim 1, wherein the nuclear detector is adapted to be moved about the region of interest during the detection of radiation.

9. The method of claim 8, wherein detected radiation from a reference radiation source provided in the region of interest is used in quantifying the actual target dose.

10. A system for determining a dose during therapy with a therapeutic substance, which comprises a therapeutic radionuclide or is radioactively labelled, the system comprising:
    a nuclear imaging system, comprising a nuclear detector and a control unit, comprising a registration module adapted for registering the nuclear detector with respect to a provided 3D image comprising at least a region of interest;
    a first database with pre-calculated simulations of detection values for a plurality of radiation distributions, and wherein the dose evaluation module is adapted for quantifying the actual target dose on the basis of the detected radiation and the pre-calculated simulations; and
    a dose evaluation module adapted for quantifying an actual target dose in a target area to be treated, by evaluating data from the nuclear detector,
    wherein quantifying in real time comprises taking into account at least one of: previous simulations with known simulated radiation distributions, previous measurements on known radiation distributions, and the radiation of a reference radiation source.

11. The system of claim 10, adapted to determine whether the actual target dose has reached at least one of: a predefined upper threshold $S_U$, and a predefined lower threshold $S_L$.

12. The system of claim 10, wherein the dose evaluation module is adapted to determine a difference between the applied radiation activity and the actual target activity, and for outputting a signal related to the difference, and/or if the difference has reached a predetermined threshold.

13. The system of claim 10, wherein the nuclear imaging system is adapted to detect Bremsstrahlung caused in the body by a therapeutic substance.

14. The system of claim 10, wherein the nuclear detector comprises:
    a. a 2D Gamma camera or a Gamma probe; or
    b. a grid of Gamma detectors, adapted to be positioned adjacent to a surface of the body.

15. The system of claim 10, further comprising a second database comprising measured radiation detection values for a variety of nuclear radiation distributions in a physical body phantom, and wherein the dose evaluation module is adapted for quantifying the actual target dose on the basis of the detected radiation and the measured radiation detection values.

16. The system of claim 10, wherein the nuclear detector is adapted to be moved about the region of interest during the detection of radiation.

17. The system of claim 16, further comprising a reference radiation source, wherein the dose evaluation module employs detected radiation from the reference radiation source in quantifying the actual target dose.

* * * * *